(12) United States Patent
Jenkins et al.

(10) Patent No.: US 6,815,670 B2
(45) Date of Patent: *Nov. 9, 2004

(54) MATERIALS AND APPARATUS FOR THE DETECTION OF CONTRABAND

(75) Inventors: Anthony Jenkins, North Reading, MA (US); William J. McGann, Raynham, MA (US); Joseph D. Napoli, Windham, NH (US); Kevin J. Perry, Pelham, NH (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/657,223

(22) Filed: Sep. 8, 2003

(65) Prior Publication Data

US 2004/0094707 A1 May 20, 2004

Related U.S. Application Data

(63) Continuation of application No. 09/411,455, filed on Oct. 1, 1999, now Pat. No. 6,642,513.
(60) Provisional application No. 60/103,168, filed on Oct. 6, 1998.

(51) Int. Cl.[7] .......................... G01N 00/00; H01J 49/00
(52) U.S. Cl. .................. 250/286; 250/288; 250/287; 250/282; 73/863.12; 73/863.23; 73/864.34
(58) Field of Search .................... 250/288, 286, 250/282, 287; 73/863.12, 863.23, 864.34

(56) References Cited

U.S. PATENT DOCUMENTS

| | | |
|---|---|---|
| 3,596,440 A | 8/1971 | Nutter et al. |
| 3,968,297 A | 7/1976 | Sauer |
| 4,045,997 A | 9/1977 | Showalter et al. |
| 4,317,995 A * | 3/1982 | Bradshaw et al. .......... 250/288 |
| 4,731,283 A | 3/1988 | Sakane et al. |
| 4,772,794 A | 9/1988 | Jenkins |
| 4,781,972 A | 11/1988 | Sakane et al. |
| 4,788,226 A | 11/1988 | Curry |
| 4,964,309 A | 10/1990 | Jenkins |
| 4,997,067 A | 3/1991 | Watts |
| 5,232,770 A | 8/1993 | Joseph |
| 5,342,434 A | 8/1994 | Wu |
| 5,405,781 A * | 4/1995 | Davies et al. .............. 436/52 |
| 5,491,337 A * | 2/1996 | Jenkins et al. ............. 250/287 |
| 5,741,984 A | 4/1998 | Danylewych-May et al. |
| 5,760,314 A | 6/1998 | Bromberg et al. |
| 5,859,362 A | 1/1999 | Neudorfl et al. |
| 5,859,375 A | 1/1999 | Danylewych-May et al. |
| 5,915,268 A | 6/1999 | Linker et al. |
| 5,922,104 A | 7/1999 | Park et al. |
| 6,169,045 B1 | 1/2001 | Pike et al. |
| 6,261,979 B1 | 7/2001 | Tanaka et al. |
| 6,375,886 B1 | 4/2002 | Angadjivand et al. |
| 6,642,513 B1 * | 11/2003 | Jenkins et al. ............. 250/288 |

FOREIGN PATENT DOCUMENTS

EP    0 247 243    of 1987

* cited by examiner

Primary Examiner—John R. Lee
Assistant Examiner—Kalimah Fernandez
(74) Attorney, Agent, or Firm—Gerald E. Hespos; Anthony J. Casella

(57) ABSTRACT

A detector requires a stream of dry air for transporting particles to the detector. The detector then operates to determine whether the dry air has transported any particles of interest. Continuous operation of the detector is permitted by providing first and second dryers that can be operated alternately for drying air that is to be directed to the detector. The dryer that is not being operated is recharged. Air is directed alternately between the first and second dryer to ensure that neither dryer is operated after reaching saturation.

25 Claims, 6 Drawing Sheets

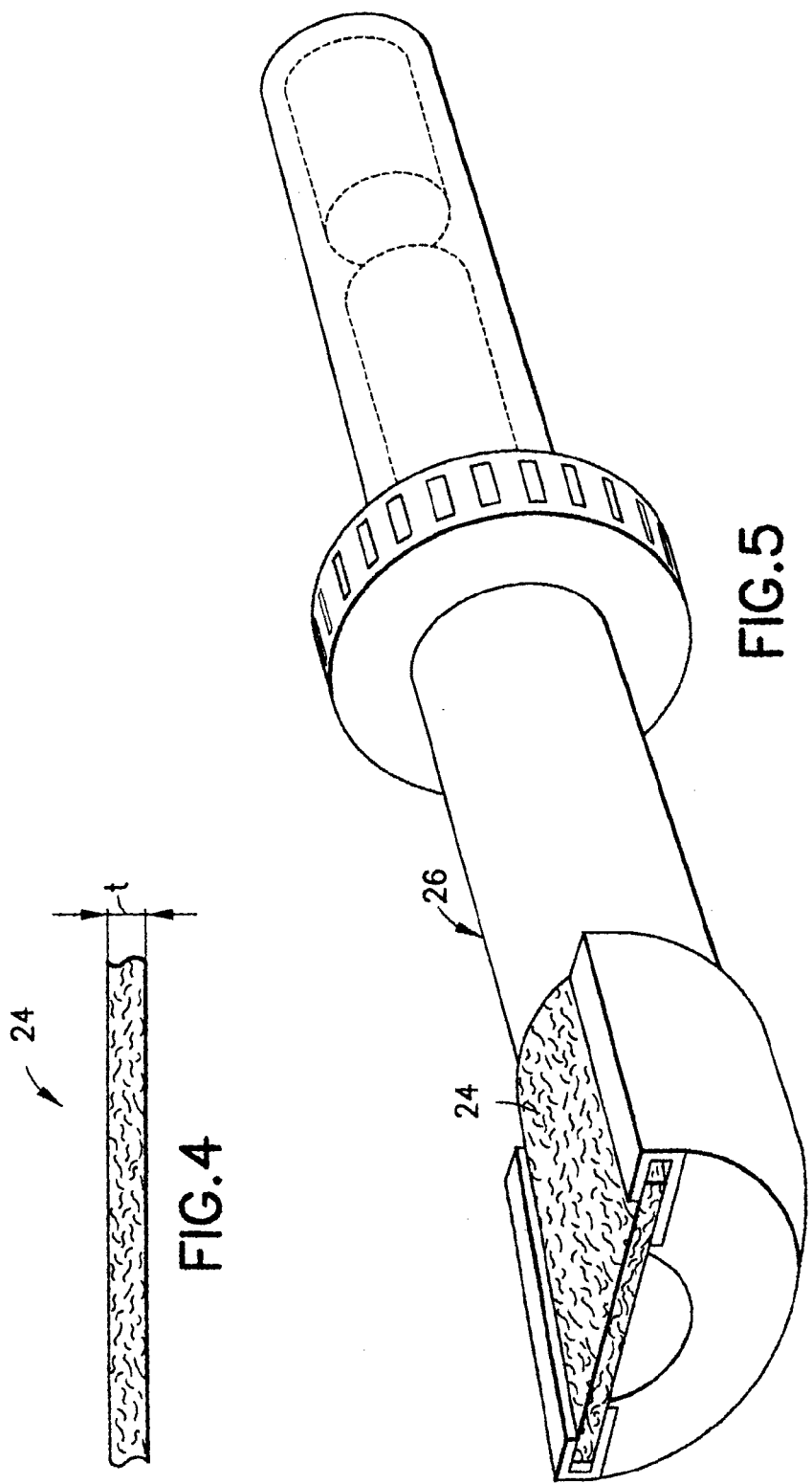

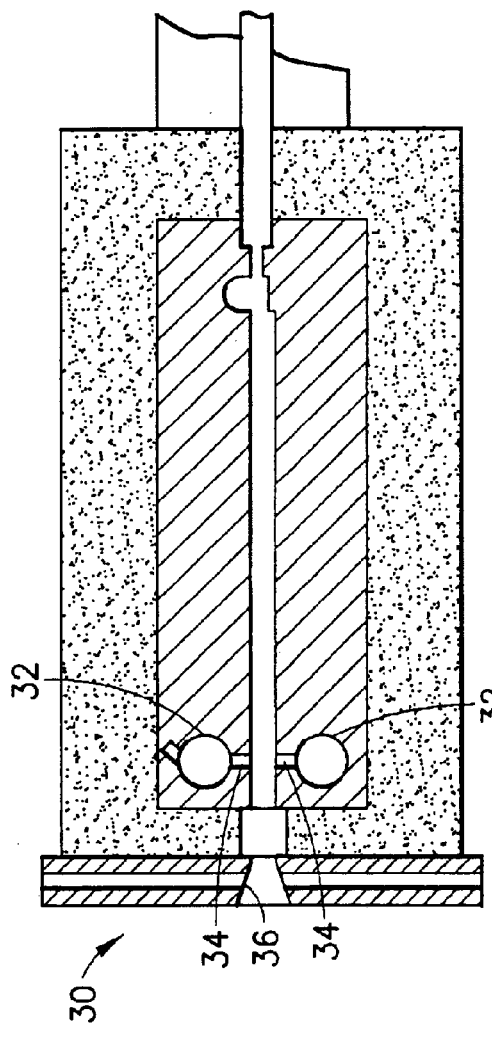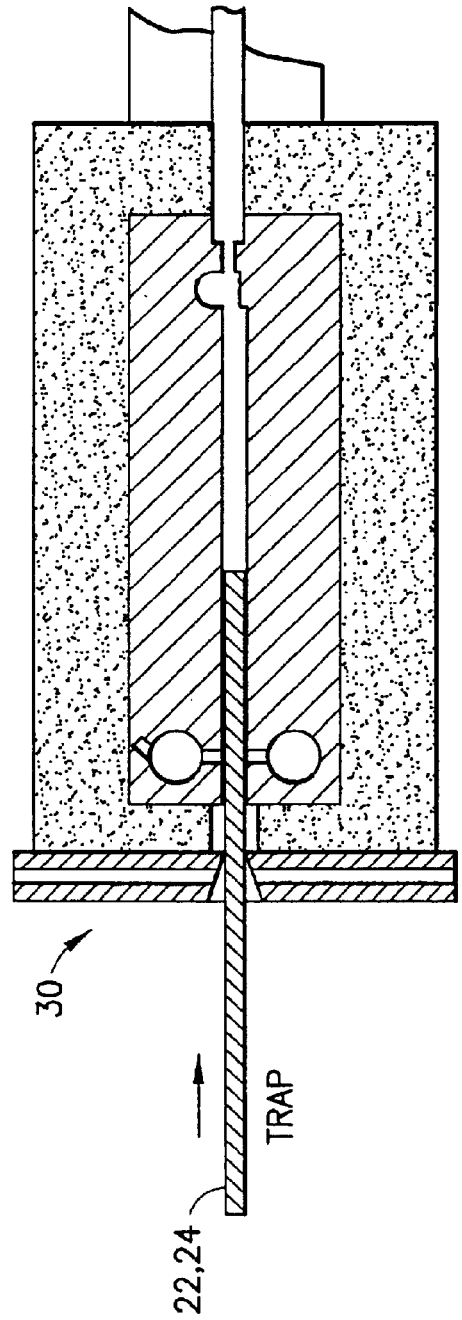

MATERIALS AND APPARATUS FOR THE DETECTION OF CONTRABAND

This application is a continuation of U.S. Patent Application Ser. No. 09/411,455 filed Oct. 1, 1999 now U.S. Pat. No. 6,642,513 which claims the benefits of 60/103,168 filed Oct. 6, 1998.

BACKGROUND OF THE INVENTION

1. Field of the Invention

The subject invention is directed to materials that can be used to collect traces of contraband. The subject invention also is directed to an apparatus for detecting trace particles and condensed vapors of contraband.

2. Description of the Related Art

Detection systems exist for detecting particulate and condensed phase traces of materials, such as narcotics and explosives. Such systems are marketed by Ion Track Instruments, Inc., which is the assignee of the subject invention. One system of Ion Track Instruments, Inc. is shown in U.S. Pat. No. 5,491,337. Other systems for these general purposes are marketed by Barringer Technologies Inc. under the name Ion Scan Detection Systems and by Intelligent Detection Systems of Canada, under the name Sirius. These prior are systems are deployed, for example, at airports to detect and prevent the introduction of explosives and to detect and deter the traffic in narcotics.

The prior art detection systems rely upon the fact that trace amounts of contraband will be transferred to the body of a person who had handled the contraband and subsequently will be transferred from the body to any article the person may be carrying (e.g., purse, suitcase, backpack, etc.). Trace amounts of contraband may be collected for analysis by wiping a small sheet-like wipe or trap across the purse, suitcase, backpack or other article of the suspect. The prior art wipe or trap then is inserted into a prior art detection apparatus which tests for the presence of certain contraband particles or vapors.

Sample wipes or traps used in such prior art detection apparatus typically have been made of paper, cotton cloth or porous PTFE (Teflon). Each of these prior art sampling media have their own shortcomings. For example, pure Teflon material has a very low coefficient of friction, and therefore does not efficiently remove small particles from rough surfaces. Paper and cotton wipes or traps, on the other hand, may pick up particles more efficiently. However, paper and cotton also pick up water. As a result, they delay the evaporation process of the target materials and inhibit the response. Therefore, prior art paper and cotton wipes or traps are not well suited for use on surfaces that may be wet. Although these prior art sample wipes are fairly efficient for detecting particulates, they are significantly less efficient for detecting vapor. In particular, Teflon is not the best vapor trap, and paper has many active sites which do not release the trapped vapor after the sample wipe has been placed in a detection apparatus.

The prior art detection systems typically rely upon a sample being collected on a sampling medium, such as the above-described sample wipes or traps. These samples may be transferred physically into the prior art detection apparatus as identified above. Alternatively, the sampling medium itself may be heated. The heat is intended to cause at least portions of the sample to be evaporated and then drawn into the detection system on an air stream. This latter prior art method generally is preferred because it allows the detection of condensed vapors which may have been collected, as well as any particulate material.

An existing system sold by Ion Track Instruments, Inc. is illustrated schematically in FIG. 1. This prior art system of FIG. 1 is similar to the system described in greater detail in the above-referenced U.S. Pat. No. 5,491,337. The prior art system of FIG. 1 analyzes samples that are collected on sample wipes consisting of a clean porous filtered paper. These wipes are dropped into a thermal desorber 12 in FIG. 1. Desorbed material is carried into the detector by the action of a sampling pump 14. The sample air is drawn into the detector 16 over a dimethyl silicone membrane 18. Some contraband or other materials of interest diffuse through the membrane 18 and into the detector 16, which may be an ion mobility spectrometer or an ion trap mobility spectrometer. The dimethyl silicone membrane 18 eliminates all dust, dirt and most atmospheric materials, including water, all of which may cause problems in the detector 16. Unfortunately, the membrane 18 is only a few percent efficient at transferring the materials of interest, and this efficiency can limit the ultimate sensitivity of the apparatus 10.

In view of the above, it is an object of the subject invention to provide a filter material for sampling vapor and particulates which enables air flow through the material for vacuum sampling.

It is another option of the subject invention to provide an efficient sample pick-up that is suitable for use on rough surfaces and that will perform well on wet surfaces.

It is another object of the subject invention to provide sample pick-up material that is low in cost and/or that is resuable.

A further object of the subject invention is to provide a detection system that retains the advantages of the prior art systems, while improving the efficiently of the transfer of materials of interest into the detector.

SUMMARY OF THE INVENTION

The subject invention is directed to an improved sampling medium for a detection system and to a detection system with improved performance.

The sampling medium of the subject invention may be an open weave glass fabric which is coated with a thin layer of Teflon. The coating is carried out in such a manner to leave spaces open between the respective fibers of the fiberglass web. Similar materials are used for specialty conveyor belts, and such conveyor belts are marketed by Greenbelt Industries. Small patches of this open weave glass fabric coated with Teflon picks up particulate matter from wet and dry surfaces simply by wiping the small patch of material across the surface. However, the prior art open weave glass fabric coated with Teflon, as used on conveyor belts, is not efficient for picking up samples of material of interest from rough or pitted surfaces. It has been found that the efficiency of pick-up can be improved significantly by roughening the surface with an abrasive to cut through the surface of the Teflon coating at a plurality of spaced-apart locations and to break some of the glass fibers free. This produces a three-dimensional surface, with the broken fibers extending angularly from the plane of the material substantially in the manner of a brush. The fibers act as a scrubbing material and pick-up small particles into the matrix. The Teflon has been found to hold the remaining weave together and to enhance durability of the sample trap.

The sample traps can be manufactured by starting with prior art open weaved glass fabric coated with Teflon and intended for the above-referenced specialty conveyor belts. The fabric then may be subjected to an abrasive action to cut through the surface of the Teflon and to break some of the glass fiber free into the above-referenced brush-like configuration. The elongate sheet of material then is subjected to punching or cutting to produce small circular or rectangular traps.

An alternate trap or wipe material is a non-woven felt fabric made of high temperature polyamide fiber. This material is more abrasive than Teflon, and therefore for many applications may not require the abrasive treatment of the above-referenced glass woven fabric that had been coated with Teflon. Additionally, the non-woven felt fabric made of high temperature polyamide fiber exhibits superior high temperature performance. The preferred embodiment is a thin sheet with a thickness of less than 3 mm. Wipes of this type have been found to allow a high flow of air when a small vacuum is applied to one side. The material retains both large and small particles, and also traps vapors from low volatility contraband, such as cocaine vapor or plastic explosives vapors. The non-woven felt fabric made of high temperature polyamide fiber also has a low thermal inertia, which allows the trap to be heated rapidly to temperatures exceeding 200° C., where most contraband of interest evaporates rapidly.

A detection system that may be used with the sample wipes described above employs a desorber to purge the sample wipe of unwanted atmospheric constituents and volatile contaminants. These unwanted atmospheric constituents, such as water vapor and oxides of nitrogen upset the detection process. This purging is achieved in the desorber by feeding dry air from a manifold above and below the sample wipe or trap through a series of small holes along the mouth of the desorber. Alternatively, the dry air may be directed through a narrow slot or through other means for creating an air curtain. The dry air passes through the wipe and purges out the ambient air. The purged air then passes to the outside atmosphere, thus creating a dry air curtain at the entry to the desorber. A portion of the dry air fed through the manifold system presses down the desorber. As the trap or wipe is introduced into the desorber, it quickly obtains the temperature of the desorber. The materials of interest evaporate and are carried on the air stream of dry air into the detector. The detector preferably is an ion mobility spectrometer or an ion trap mobility spectrometer as described above with reference to FIG. 1 and as described in significantly greater detail in U.S. Pat. No. 5,491,337.

In another embodiment, the trap or wipe is operated by an automated actuator. The actuator pushes the trap in and out of the desorber, but does not pull it completely out. In the outer position, a high flow of air is drawn through the trap by the action of a vacuum pump. Any material which is drawn into the trap, is captured, and subsequently introduced into the desorber by actuating the trap into the desorber. The material captured by the trap is evaporated in the desorber as described above, and is passed into the detector.

The above-described trap system can be incorporated into a walk-through configuration. In this latter embodiment, air is allowed to flow over the subject's body either horizontally or vertically. For example, the trap can be disposed in a portal through which the subject may move. Preferably, the trap is disposed at a location in the portal vertically above the subject. The air then is caused to flow through the trap mounted near the test subject by the action of a suction pump. All vapors and particles entrained in the air sample are trapped in the trap and subsequently are detected.

The trap material in this latter embodiment traps samples only from an air stream, and is not used to wipe surfaces. This gives an opportunity for using trap materials which may otherwise be too abrasive. An example of a suitable material is a stainless steel filter material, which provides good trapping efficiency for vapors, as well as good trapping of particles.

BRIEF DESCRIPTION OF THE DRAWINGS

FIG. 4 is a side elevational view of a second embodiment of a trap.

FIG. 5 is a perspective view of a vacuum sampler employing the trap of FIG. 4.

FIG. 6 is a cross-sectional view of a describer for use in a detection system, such as the detection system of FIG. 1.

FIG. 7 is a side elevation view similar to FIG. 6, but showing the sample trap being inserted into the desorber.

DETAILED DESCRIPTION OF THE PREFERRED EMBODIMENTS

Figure 3:
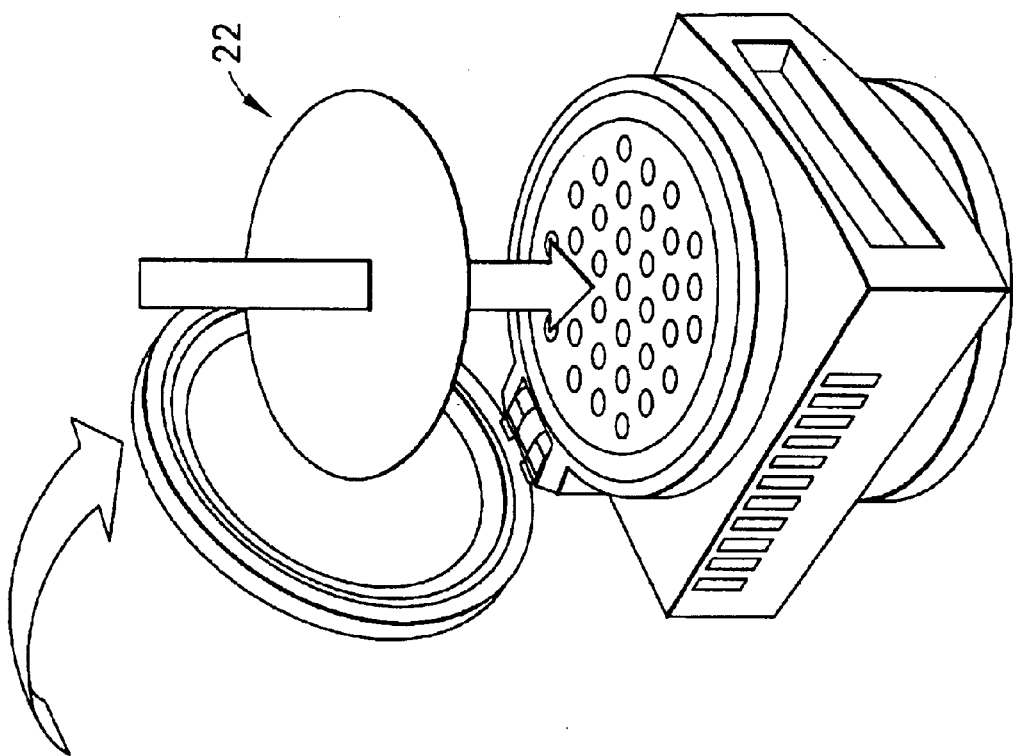
FIG. 3 is a perspective view showing the trap being placed in a detection apparatus.
Figure 2:
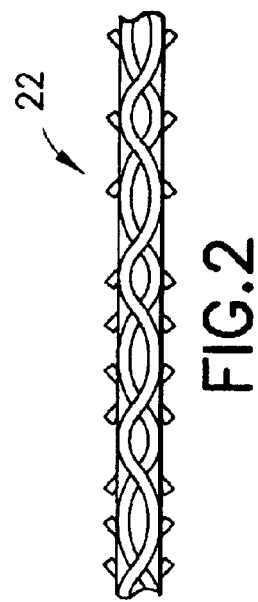
FIG. 2 is a side elevational view of a trap in accordance with a first embodiment of the subject invention.

A sample trap in accordance with a first embodiment of the subject invention is identified generally by the numeral 22 in FIGS. 2 and 3. The sample trap 22 is formed from an open weave glass fabric coated with a thin layer of PTFE (Teflon). The weaving and coating is carried out such that open spaces are defined between the elements of the fiberglass web. The initial product may be a conveyor belt, such as the specialty conveyor belts marketed by Greenbelt Industries. However, the open weave glass fabric coated with Teflon and used for specialty conveyor belts is roughened with an abrasive material to cut through the surface of the Teflon at selected locations on the woven fiberglass fabrics and to break some of the glass fibers free. Thus, as shown schematically in FIG. 2, short sections of glass fibers will be directed away from the plane of the fabric in substantially the manner of a brush. These broken fibers act as a scrubbing material and pick up small particles into the matrix for subsequent analysis in a detection apparatus as explained further herein. The roughened woven glass fabric then is subjected to a punching or cutting operation to produce small sample traps that are appropriately configured and dimensioned for the particular detection apparatus. More specifically, as shown in FIG. 3, the roughened coated glass fabric has been punched into the circular sample trap. In other embodiments, the fabric may be cut into rectangular squares.

An alternate embodiment of the subject sample trap is identified generally by the numeral 24, and is illustrated schematically in FIG. 4. This alternate trap is a non-woven felt fabric made of a high temperature polyamide fiber. The trap 24 has a thickness "t" as shown in FIG. 4 of less than 3 mm, and preferably in the range of approximately 1–2 mm. This material allows a high flow of air when a small vacuum is applied to one side of the trap 24. The material is more abrasive then a Teflon fabric, and therefore retains both large and small particles and also traps vapors from low volatility contraband, such as cocaine vapor and plastic explosives vapors. The non-woven high temperature polyamide fiber of the trap 24 has a superior high temperature performance and a low thermal inertia. The low thermal inertia allows the trap 24 to be heated rapidly to temperatures exceeding 200° C., which is a temperature where most contrabands of interest evaporate rapidly. The sample trap 24 may be used in an apparatus substantially in the manner shown in FIG. 3 above. Alternatively, the trap 24 may be cut into a rectangular shape and may be used in a hand-held vacuum sampler 26, as shown in FIG. 5.

Figure 1:
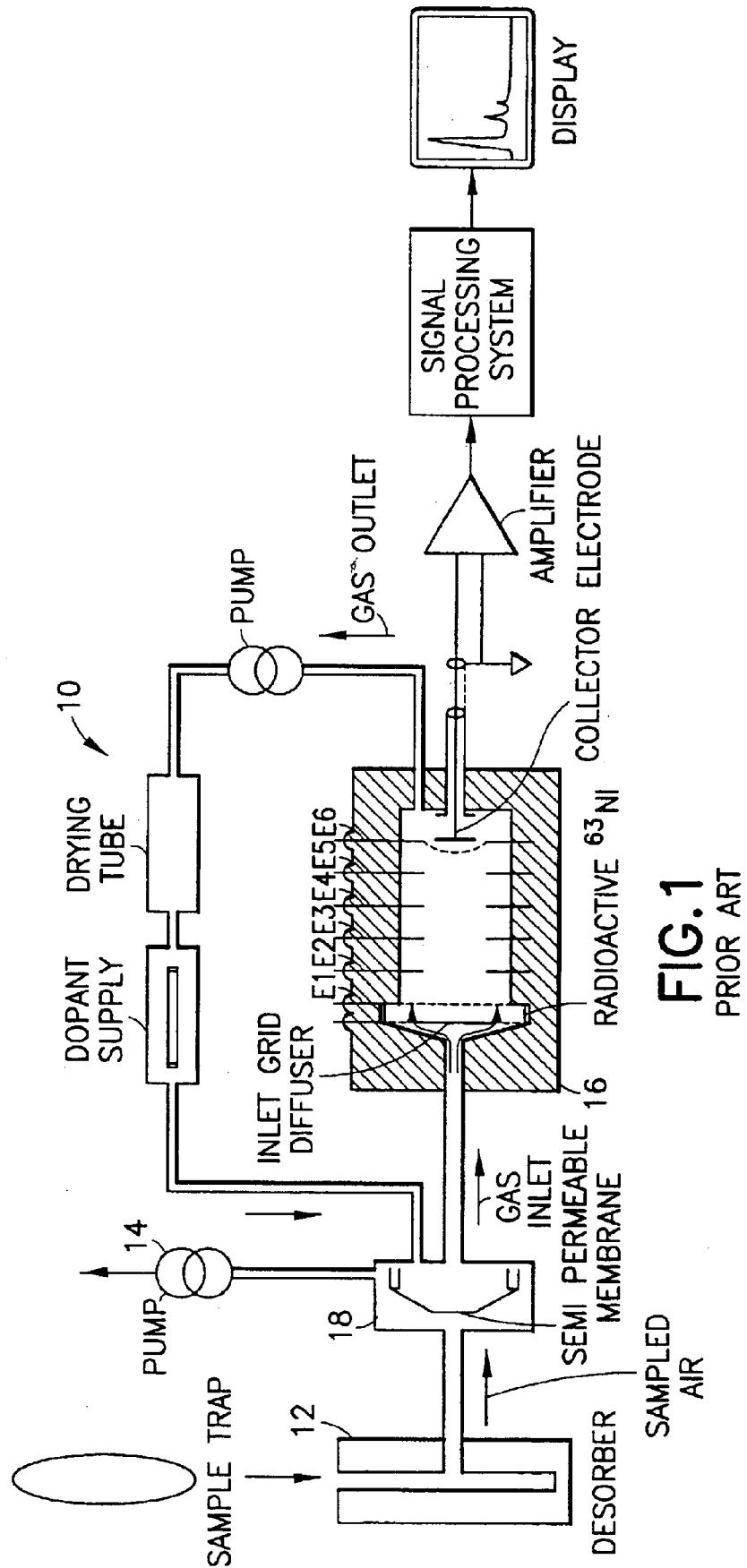
FIG. 1 is a schematic view of a prior art ion trap mobility spectrometer.
Figure 8:
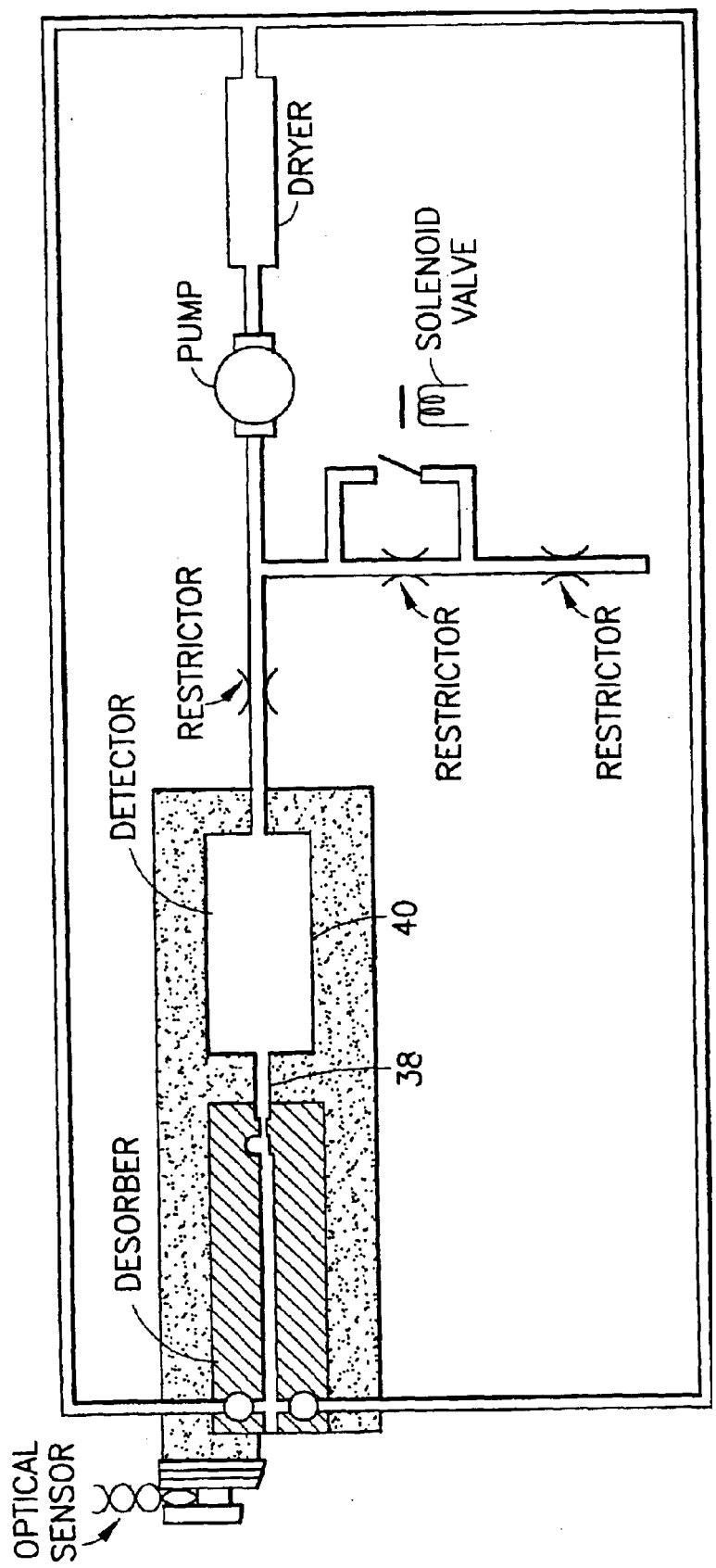
FIG. 8 is a schematic view of the desorber of FIGS. 6 and 7 incorporated into a detection system.

The trap 22 or the trap 24 described and illustrated above may be used in the prior art detection system described above and illustrated in FIG. 1, or in other prior art systems. Alternatively, the sample traps 22 and 24 may be used in a more efficient system that includes a heated desorber as shown, for example, in FIGS. 6 and 7 and as identified generally by the numeral 30. The desorber 30 causes the sample trap 22 or 24 to be purged of unwanted atmospheric constituents, such as water vapor or oxides of nitrogen. More particularly, the sample trap 22 or 24 is pushed into the desorber 30 as shown in FIG. 7. Dry air is fed from the manifold 32 above and below the sample trap through a series of small holes 34 along the mouth 36 of the desorber 30. The dry air passes through the trap 22, 24 and purges out the ambient air in the trap. The purged air passes to the outside atmosphere, thus creating a dry air curtain at the entry to the desorber 30. A portion of the dry air flow fed through the manifold system 32 passes down the desorber 30. As the trap 22, 24 is introduced into the desorber 30, it quickly attains the temperature of the desorber 30. Materials picked up on the trap 22, 24 evaporate and are carried on the stream of dry air into the outlet 38 leading to the detector 40 as shown in FIG. 8. The detector 40 which is illustrated schematically in FIG. 8 may be an ion mobility spectrometer of an ion trap mobility spectrometer as shown in FIG. 1 and as described in greater detail in the above-referenced U.S. Pat. No. 5,491,337.

The trap 22, 24 may be moved relative to the desorber 30 by an automatic actuator. The actuator may push the trap 22, 24 in and out of the desorber 30, but does not entirely eject the trap 22, 24. In the out position of the trap 22, 24, a high flow of air is drawn through the trap 22, 24 by the action of a vacuum pump. Any material which is drawn into the trap is captured and subsequently introduced into the desorber 30 by actuating the trap into the desorber. The material captured by the trap 22, 24 is evaporated in the desorber 30, as described above, and is passed into the detector 40. In this embodiment, the trap system can be incorporated into a walk-through configuration. Here, air may flow over the subject's body, either horizontally or vertically. The air then may be caused to flow through the trap mounted near the test subject, by the action of a suction pump. Vapors and particles entrained in the air sample are trapped in the trap 22, 24 and subsequently are detected as described above and in U.S. Pat. No. 5,491,337.

The apparatus described above with reference to FIGS. 5–8, is particularly useful for the traps 22 and 24 of the subject invention. However, prior art traps also may be employed. Additionally, the walk through the detector described above does not require the trap to be wiped across the surface of the article or subject being tested. Hence, the trap may be formed from a material that could be too abrasive for wiping on a surface. For example, a stainless steel filter material may be used with a walk through trap, including a desorber as described above. The stainless steel filter material provides good trapping efficiency for vapors, as well as good trapping of particles.

Figure 9:
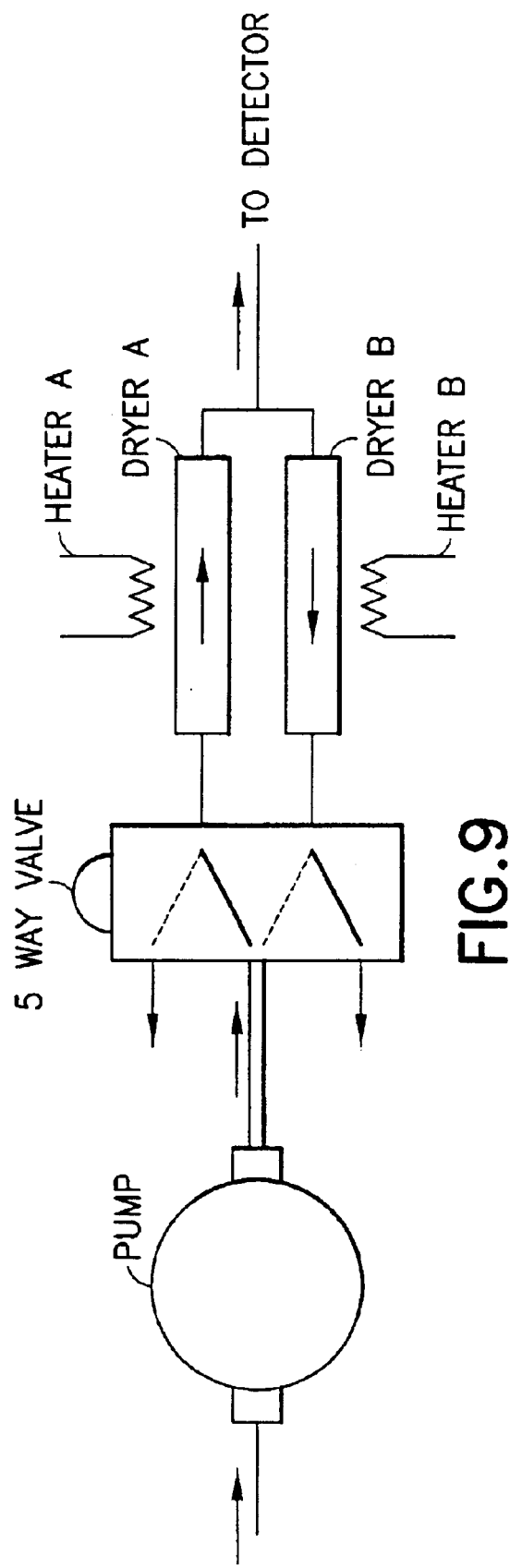
FIG. 9 is a schematic view of a dryer system.

In a further embodiment, the drying material may be recycled automatically by employing two drying tubes as shown in FIG. 9. In the position shown in FIG. 9, a five way valve directs air from the pump through the dryer bed A and to the detector system. Some of this air is directed in the reverse direction through dryer B. At the same time, dryer B is heated by a small heater to a temperature exceeding 100° C. Water is liberated from the dryer and escapes to atmosphere through the five way valve. After a time sufficient to dry most of the water from dryer B, the heater thereof is switched off, and the temperature of dryer B is allowed to fall back to ambient. After a further interval, but before dryerA becomes saturated, the five way valve is switched, thus reversing the flows. Dryer B becomes the active dryer, while dryer A is heated and reactivated. The entire process is either regulated by a timer or by a measure of the humidity of the air being circulated. This cycle may be measured by the detector itself.

What is claimed is:

1. A detector apparatus comprising: a detector for detecting trace amounts of particles of interest carried on a stream of air; two dryers in communication with the stream of air; at least one valve in communication with the dryers for selectively placing a first of the dryers in communication with the detector; and at least one heater for selectively recharging a second of the dryers while the first dryer is in communication with the detector.

2. The apparatus of claim 1, wherein the valve is a five-way valve for directing a first portion of dried air produced by the dryer that is in communication with the detector towards the detector while directing a second portion of the dried air from the dryer that is in communication with the detector toward the other of the dryers for transporting moisture from the other dryer.

3. The apparatus of claim 1, wherein the detector is an ion trap mobility spectrometer.

4. The apparatus of claim 1, further comprising a timer connected to the valve for alternately placing the first and second dryers in communication with the detector after a selected time.

5. The apparatus of claim 1, further comprising a humidity measurer for measuring humidity in the stream of air, the humidity measurer being operative to operate the valve at a selected humidity level.

6. The apparatus of claim 1, wherein the heater is operative for selectively heating the dryers to a temperature greater than 100° C.

7. The apparatus of claim 1, wherein the at least one heater comprises first and second heaters for selectively heating the first and second dryers respectively.

8. The apparatus of claim 1, wherein each of the dryers is operative for removing moisture from the stream of air and wherein each of the heaters is operative for heating the dryers sufficiently for vaporizing moisture collected in the respective dryer so that the vaporized moisture can be purged from the respective dryer.

9. A detector apparatus comprising: a detector for detecting trace amounts of particles of interest carried on a stream of air; two dryers in communication with the stream of air for removing moisture from the stream of air, such that each said dryer produces a stream of substantially dry air; at least one valve in communication with the dryers for selectively placing a first of the dryers in communication with the detector; and two heaters associated respectively with the dryers for heating the dryers sufficiently for vaporizing moisture collected therein and enabling the vaporized moisture to be purged from the respective dryer, whereby the dryer and heaters are operated alternately for enabling a substantially continuous stream of dried air to be in communication with the detector and enabling substantially continuous operation of the detector.

10. The apparatus of claim 9, further comprising a timer connected to the valve for alternately placing the first and second dryers in communication with the detector after a selected time.

11. The apparatus of claim 9, further comprising a humidity measurer for measuring humidity in the stream of air, the humidity measurer being operative to operate the valve at a selected humidity level.

12. A detector apparatus having a detector for detecting trace amounts of materials of interest carried into the detector through a detector inlet on a stream of air, the detector apparatus comprising traps formed from a material for collecting said materials of interest, a desorber having an inlet for communicating with one of the traps to be tested for the materials of interest and an outlet communicating with the detector inlet, the desorber including a manifold communicating with the inlet to the desorber for directing air from the manifold and across the inlet to the desorber, a heater for heating the desorber to evaporate any of the materials of interest on the trap, a pump for carrying the materials of interest on the air and into the detector; and a dryer assembly for drying air directed into the desorber, the dryer assembly comprising at least first and second dryers and at least one valve for selectively placing one of the first and second dryers in communication with the desorber while substantially isolating the other of the first and second dryers from the desorber.

13. The apparatus of claim 12, further comprising first and second heaters in proximity to the respective first and second dryers and being selectively operable for recharging the dryers.

14. The apparatus of claim 13, wherein the detector is an ion mobility spectrometer.

15. The apparatus of claim 13, wherein the detector is an ion trap mobility spectrometer.

16. The apparatus of claim 13, wherein the inlet of the desorber has a plurality of small holes for directing dry air from the manifold.

17. The apparatus of claim 13, further comprising a timer connected to the valve for alternately placing the first and second dryers in communication with the detector after a selected time.

18. The apparatus of claim 13, further comprising a humidity measurer for measuring humidity in the stream of air, the humidity measurer being operative to operate the valve at a selected humidity level.

19. The apparatus of claim 13, wherein the inlet to the desorber is a narrow slot.

20. A method for continuously operating a detector for detecting particles of interest, said method comprising:
   operating one of first and second dryers for defining an operated dryer and a non-operated dryer;
   directing a stream of air through the operated dryer for transferring moisture from the stream of air to the operated dryer to produce a stream of dry air;
   directing the stream of dry air from the operated dryer toward an object to be tested for particles of interest and then toward the detector;
   recharging the non-operated dryer; and
   switching the stream of air from one of the dryers to the other after the non-operated dryer has been at least partially recharged and before the operated dryer has become saturated.

21. The method of claim 20, wherein the switching step is carried out after passage of a selected period of time.

22. The method of claim 20, wherein the switching step is carried out based on a measurement of moisture in the stream of dry air.

23. The method of claim 20, wherein the re-charging step comprises heating the non-operated dryer to a temperature of at least 100° C.

24. A method for continuously operating a detector for detecting whether an object has any particles of interest, said method comprising:
   operating a first dryer;
   directing a stream of air through the first dryer for transferring water from the stream of air to the first dryer;
   recharging a second dryer for purging water from the second dryer while the stream of air is directed through the first dryer; and
   redirecting the stream of air through the second dryer after the second dryer has been at least partly recharged and before the first dryer has become saturated with water; and
   recharging the first dryer while the stream of air is directed through the second dryer.

25. A method for continuously operating a detector for detecting particles of interest, said method comprising:
   operating a first dryer for producing a first flow of dried air;
   directing a first portion of the first flow of dried air towards the detector for delivering potential particles of interest into the detector;
   directing a second portion of the first flow of dried air through a second dryer and simultaneously heating the second dryer sufficiently for liberating water from the second dryer;
   terminating the first flow of dried air from the first dryer and operating the second dryer for producing a second flow of dried air;
   directing a first portion of the second flow of dried air towards the detector for transporting potential particles of interest into the detector;
   diverting a second portion of the second flow of dried air from the second dryer to the first dryer and simultaneously heating the first dryer for liberating moisture from the first dryer, whereby the first and second dryers are operated sequentially prior to either of the first and second dryers being saturated for permitting continuous operation of the detector.

* * * * *

(12) EX PARTE REEXAMINATION CERTIFICATE (10369th)
United States Patent
Jenkins et al.

(10) Number: US 6,815,670 C1
(45) Certificate Issued: *Oct. 30, 2014

(54) MATERIALS AND APPARATUS FOR THE DETECTION OF CONTRABAND

(75) Inventors: Anthony Jenkins, North Reading, MA (US); William J. McGann, Raynham, MA (US); Joseph D. Napoli, Windham, NH (US); Kevin J. Perry, Pelham, NH (US)

(73) Assignee: Morpho Detection, Inc., Newark, CA (US)

Reexamination Request:
No. 90/013,012, Oct. 2, 2013

Reexamination Certificate for:
Patent No.: 6,815,670
Issued: Nov. 9, 2004
Appl. No.: 10/657,223
Filed: Sep. 8, 2003

(*) Notice: This patent is subject to a terminal disclaimer.

Related U.S. Application Data

(63) Continuation of application No. 09/411,455, filed on Oct. 1, 1999, now Pat. No. 6,642,513.

(60) Provisional application No. 60/103,168, filed on Oct. 6, 1998.

(51) Int. Cl.
*H01J 49/00* (2006.01)

(52) U.S. Cl.
USPC ........... 250/286; 250/288; 250/287; 250/282; 73/863.12; 73/863.23; 73/864.34

(58) Field of Classification Search
None
See application file for complete search history.

(56) References Cited

To view the complete listing of prior art documents cited during the proceeding for Reexamination Control Number 90/013,012, please refer to the USPTO's public Patent Application Information Retrieval (PAIR) system under the Display References tab.

*Primary Examiner* — Angela M Lie

(57) ABSTRACT

A detector requires a stream of dry air for transporting particles to the detector. The detector then operates to determine whether the dry air has transported any particles of interest. Continuous operation of the detector is permitted by providing first and second dryers that can be operated alternately for drying air that is to be directed to the detector. The dryer that is not being operated is recharged. Air is directed alternately between the first and second dryer to ensure that neither dryer is operated after reaching saturation.

Attention is directed to the decision of *Morpho Detection Inc v. Smiths Detection Inc*, 211cv00498 (USDC VA Eastern-Norfolk); verdict in favor of Morpho Detection (plaintiff), entered on 12/11/2012. This reexamination may not have resolved all questions raised by this decision. See 37 CFR 1.552(c) for *ex parte* reexamination and 37 CFR 1.906(c) for *inter partes* reexamination.

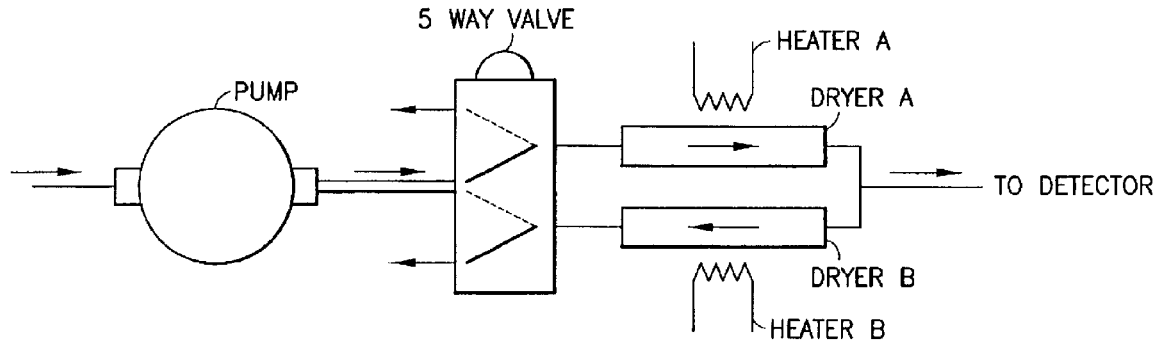

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 12-14, 16-17 and 19 is confirmed.

Claims 1, 4, 6-10, 20-21 and 23-25 are cancelled.

Claims 2, 3, 5, 11, 15, 18 and 22 were not reexamined.

* * * * *